(12) United States Patent
Rich

(10) Patent No.: US 12,109,202 B2
(45) Date of Patent: Oct. 8, 2024

(54) FIXED DOSE COMBINATION OF CHOLINESTERASE INHIBITOR AND A QUATERNARY AMMONIUM ANTIMUSCARINIC AGENT TO TREAT NEURODEGENERATIVE COGNITIVE DISORDERS

(71) Applicant: QAAM Pharmaceuticals, LLC, Canandaigua, NY (US)

(72) Inventor: Steven A Rich, Canandaigua, NY (US)

(73) Assignee: QAAM Pharmaceuticals, LLC, Canandaigua, NY (US)

( * ) Notice: Subject to any disclaimer, the term of this patent is extended or adjusted under 35 U.S.C. 154(b) by 446 days.

(21) Appl. No.: 17/163,010

(22) Filed: Jan. 29, 2021

(65) Prior Publication Data

US 2022/0241254 A1 Aug. 4, 2022

(51) Int. Cl.

| A61K 31/438 | (2006.01) |
|---|---|
| A61K 9/00 | (2006.01) |
| A61K 9/48 | (2006.01) |
| A61K 9/70 | (2006.01) |
| A61K 31/165 | (2006.01) |
| A61K 31/4015 | (2006.01) |
| A61P 25/28 | (2006.01) |

(52) U.S. Cl.
CPC .......... *A61K 31/438* (2013.01); *A61K 9/0053* (2013.01); *A61K 9/4825* (2013.01); *A61K 9/4866* (2013.01); *A61K 9/7023* (2013.01); *A61K 31/165* (2013.01); *A61K 31/4015* (2013.01); *A61P 25/28* (2018.01)

(58) Field of Classification Search
CPC .............................. A61P 25/02; A61K 9/4808
See application file for complete search history.

(56) References Cited

U.S. PATENT DOCUMENTS

| 5,346,906 | A | 9/1994 | Baker et al. |
| 5,861,431 | A | 1/1999 | Hildebrand et al. |
| 6,063,808 | A | 5/2000 | Fabiano et al. |
| 6,204,285 | B1 | 3/2001 | Fabiano et al. |
| 6,255,502 | B1 | 7/2001 | Penkler et al. |
| 7,091,236 | B1 | 8/2006 | Roberts et al. |
| 8,343,467 | B2 | 1/2013 | Woehrmann et al. |
| 8,404,701 | B2 | 3/2013 | Chase et al. |
| 8,877,768 | B2 | 11/2014 | Chase et al. |
| 8,969,402 | B2 * | 3/2015 | Rich .................... A61K 9/7023 514/319 |
| 9,561,218 | B2 | 2/2017 | Clarence-Smith et al. |
| 2003/0225031 | A1 | 12/2003 | Quay |
| 2004/0082644 | A1 | 4/2004 | Korsten et al. |
| 2006/0018839 | A1 | 1/2006 | Ieni et al. |
| 2006/0142241 | A1 | 6/2006 | Yoo |
| 2011/0086950 | A1 | 4/2011 | Changping |
| 2011/0201597 | A1 | 8/2011 | Chase et al. |
| 2014/0350281 | A1 | 11/2014 | Demattei et al. |
| 2015/0086640 | A1 | 3/2015 | Staniforth et al. |
| 2018/0042922 | A1 | 2/2018 | Cheruvu et al. |
| 2019/0000826 | A1 | 1/2019 | Clarence-Smith et al. |
| 2019/0314332 | A1 | 10/2019 | Rich |

FOREIGN PATENT DOCUMENTS

WO 2009052353 A2 4/2009

OTHER PUBLICATIONS

Capsule-in-Capsule Technology W.J. Bowtle Pharmaceutical Technology vol. 2010 Supplement, Issue 6 (Year: 2010).*
A Comparative Study of Efficacy and Safety of Ondansetron, Glycopyrrolate and Dexamethasone for Post Operative Nausea and Vomiting Following General Aneasthesia Ragi Jain and Rashmi Sharma Anesth Essays Res. 2015 (Year: 2015).*
Domperidone is effective in the prevention of rivastigmine-related gastrointestinal disturbances Leonardo Scarzella, Alessandra Costanza, Katia Vastola Functional Neurology 2007 (Year: 2007).*
Adherence to Medication in Patients with Dementia Arlt et al. Drugs Aging 2008; 25 (12): 1033-1047 (Year: 2008).*
International Search Report for PCT/US22/12963, dated Apr. 1, 2022.
Mclachlan A, et al. "Meals and Medicines" Australian Prescriber Apr. 1, 2006, vol. 29, pp. 40-42, DOI: 10.18773/austprescr.2006.026; p. 41, table 1, footnote.
Tsao et al., "Transient Memory Impairment and Hallucinations Associated with Tolterodine Use", New England Journal of Medicine, vol. 349, pp. 2274-2275, 2003.
Van Eijk et al., "Effect of rivastigmine as an adjunct to usual care with haloperidol on duration of delirium and mortality in critically ill patients: a multicentre, double-blind, placebo-controlled randomised trial", Lancet, vol. 376, pp. 1829-1837, 2010.
Verdejo et al. Anales de Medicina, 1992, vol. 9, No. 3, abstract only.
VESICARE® (solifenacin succinate) tablets, Product Information Sheet, 16 pages, 2010.
Williams et al., "Survival and mortality differences between dementia with Lewy bodies vs Alzheimer disease", Neurology, vol. 67, pp. 1935-1941, 2006.
Aarsland et al. "Role of cholinesterase inhibitors in Parkinson's disease anddementia with Lewy bodies."; J Geriatr Psychiatry Neurol. Sep. 2004;17(3):164-71.
Alcalde et al. "A Simple Halide-to-Anion Exchange Method for Heteroaromatic Salts and Ionic Liquids", Laboratory of Organic Chemistry, Faculty of Pharmacy, University of Barcelona; Apr. 2012.

(Continued)

*Primary Examiner* — Jeffrey S Lundgren
*Assistant Examiner* — Eric Tran
(74) *Attorney, Agent, or Firm* — Brown & Michaels, PC

(57) ABSTRACT

The present invention includes a method for improving cognitive function in a human suffering from a neurodegenerative cognitive disorder. The method comprises administering to a patient a total daily dose of a cholinesterase inhibitor and a quaternary ammonium antimuscarinic compound. The total daily dose is divided into one or more doses administered before food intake. The quaternary ammonium antimuscarinic compound is administered in a first drug delivery element configured for rapid absorption into a body of the patient, and the cholinesterase inhibitor is administered in a second drug delivery element configured for a slower or delayed absorption into the body of the patient.

5 Claims, 3 Drawing Sheets

(56) References Cited

OTHER PUBLICATIONS

Ancelin et al., "Non-degenerative mild cognitive impairment in elderly people and use of anticholinergic drugs: longitudinal cohort study", BMJ, doi:10.1136/bmj.38740.439664.DE, 5 pages, 2006.
Aschenbrenner et al., Drug Therapy in Nursing, p. 324, 2009.
Campbell et al., "Use of anticholinergics and the risk of cognitive impairment in an African American population", Neurology, vol. 75, pp. 152-159, 2010.
Carnahan et al., "The Concurrent Use of Anticholinergics and Cholinesterase Inhibitors: Rare Event or Common Practice?", JAGS vol. 52, pp. 2082-2087, 2004.
Chew et al., "Serum Anticholinergic Activity and Cognition in Patients with Moderate-to-Severe Dementia", Am. J. Geriatr. Psychiatry, vol. 13, pp. 535-538, 2005.
Collomb et al., "Composition of fatty acids in cow's milk fat produced in the lowlands, mountains and highlands of Switzerland using high-resolution gas chromatography," International Dairy Journal 12 (2002) 649-659.
Cooke et al., "Glycopyrrolate in Bladder Dysfunction", South African Medical Journal, vol. 63, p. 3, 1983.
Cummings, J. "Cholinesterase inhibitors for treatment of dementia associated with Parkinson's disease", J Neurol Neurosurg Psychiatry. Jul. 2005;76(7):903-4.
CUVPOSA (glycopyrrolate) oral solution, Product Information Sheet, pp. 6-15, 2010.
DETROL® LA (tolterodine tartrate) capsules, Product Information Sheet, 12 pages, 2008.
Douaud et al., "Preventing Alzheimer's disease-related gray matter atrophy by B-vitamin treatment", PNAS, vol. 110, pp. 9523-9528, 2013.
Drinka, "Antimuscarinic Drugs for Overactive Bladder and Their Potential Effects on Cognitive Function in Older Patients", JAGS, vol. 54, pp. 1004-1005, 2006.
ENABLEX® (darifenacin) tablets, Product Information Sheet, 16 pages, 2010.
EXELON® Capsule, Product Information Sheet, Novartis, 4 pages, 2002.
EXELON® Patch (rivastigmine transdermal system), Product Information Sheet, LTS Lohmann Therapie Systems AG, 12 pages, 2000.
Ferguson, "Modulation of lymphatic smooth muscle contraction responses by the endothelium", Journal of Surgical Research, vol. 52, pp. 359-363, 1992.
Gish et al., "Memorandum: Age-dependent manifestations of central anticholinergic effects", Department of Health and Human Services Public Health Service Food and Drug Administration Center for Drug Evaluation and Research, 30 pages, 2007.
Hashimoto et al., "Urinary Incontinence: an Unrecognised Adverse Effect with Donepezil", The Lancet, vol. 356, p. 568, 2000.
Iliff et al., "A Paravascular Pathway Facilitates CSF Flow Through the Brain Parenchyma and the Clearance of Interstitial Solutes, Including Amyloid β". Sci. Transl. Med., vol. 4(147):147ra111, 11 pages, 2012.
International Search Report and Written Opinion dated Sep. 2, 2016, International Application No. PCT/US2016/035967.
Janos et al., "Overactive bladder medicines and cognitive testing", Int. J. Clin. Pract., vol. 62, pp. 1637-1642, 2008.
Jewart et al., "Cognitive, Behavioral and Physiological Changes in Alzheimer Disease Patients as a Function of Incontinence Medications", Am. J. Geriatr. Psychiatry, vol. 13, pp. 324-328, 2005.
Jhee et al., "Centrally Acting Antiemetics Mitigate Nausea and Vomiting in Patients with Alzheimer's Disease Who Receive Rivastigmine", Clinical Neuropharmacology, vol. 25, pp. 122-123, 2002.
Kay et al., "Antimuscarinic Drugs for Overactive Bladder and Their Potential Effects on Cognitive Function in Older Patients", JAGS, vol. 53, pp. 2195-2201, 2005.
Kay et al., "Preserving cognitive function for patients with overactive bladder: evidence for a differential effect with darifenacin", Int. J. Clin. Pract., vol. 62, pp. 1792-1800, 2008.
Khullar et al., "Prevalence of Faecal Incontinence among Women with Urinary Incontinence", Br. J. Obstet. Gynaecol., vol. 105, pp. 1211-1213, 1998.
Levin et al., "Direct Measurement of the Anticholinergic Activity of a Series of Pharmacological Compounds of the Canine and Rabbit Urinary Bladder", J. Urology, vol. 128, pp. 396-398, 1982.
Lopez et al., "Predictors of progression in patients with AD and Lewy bodies", Neurology, vol. 54, pp. 1774-1779, 2000.
Mashour et al. Science Translational Medicine, 2011, vol. 3, Iss. 114, Abstract.
McKeith et al. "Efficacy of rivastigmine in dementia with Lewy bodies: a randomised, double-blind, placebo-controlled international study"; The Lancet, vol. 356, Dec. 2000.
Medline Plus, "Stress incontinence: MedlinePluss Medical Encyclopedia", available at http://www.nlm.nih.gov/medlineplus/ency/article/000891.htm, 5 pages, 2009.
Nelson et al. "Acetylcholinesterase Inhibitor Treatment is Associated with Relatively Slow Cognitive Decline in Patients with Alzheimer's Disease and AD + DLB", J Alzheimers Dis. Jan. 2009; 16(1): 29-34.
Oken, "Antihistamines, a Possible Risk Factor for Alzheimer's Disease", Medical Hypotheses, vol. 44, pp. 47-48, 1995.
Olichney et al., "Cognitive Decline is Faster in Lewy Body Variant than in Alzheimer's Disease", Neurology, vol. 51, pp. 351-357, 1998.
Ono Pharmaceutical Co., Ltd., "Launch of Rivistach® Patch, for the Treatment of Dementia of Alzheimer's Type", 2 pages, 2011.
Pagano et al. "Cholinesterase inhibitors for Parkinson's disease: a systematic review and meta-analysis."; J Neurol Neurosurg Psychiatry. Jul. 2015;86(7):767-73.
Pubchem Open Chemistry Database, 2005, Compound Summary for CID 11693, Glycopyrrolate, retrieved from https://pubchem.ncbi.nlm.nih.gov/compound/glycopyrrolate.
Ray et al. "Central Anticholinergic Hypersensitivity in Aging", Journal of Geriatric Psychiatry and Neurology, vol. 5, pp. 72-77, 1992.
AMO, R DRcaps® Capsules Achieve Delayed Release Properties for Nutritional Ingredients in Human Clinical Study, 2014, BAS 420, Capsugel Belgium NV, Printed in France.
Robert, P.H. L'Encephale, Nov. 1999, Spec. No. 5, Abstract.
Robinul® glycopyrrolate tablets, Product Information Sheet, 4 pages, 2010.
Roe et al., "Use of Anticholinergic Medications by Older Adults with Dementia", JAGS, vol. 50, pp. 836-842, 2002.
Rudolph et al., "The Anticholinergic Risk Scale and Anticholinergic Adverse Effects in Older Persons", Arch. Intern. Med., vol. 168, pp. 508-513, 2008.
SANCTURA® (trospium chloride), Product Information Sheet, 12 pages, 2011.
Sarter et al. "Developmental origins of the age-related decline in cortical cholinergic function and associated cognitive abilities"; Neurbiology of Aging 25; 2004.
Simard et al., "Locating high-affinity fatty acid-binding sites on albumin by x-ray crystallography and NMR spectroscopy," PNAS, 2005, 102(50), 17958-17963.
Sink et al., "Dual Use of Bladder Anticholinergics and Cholinesterase Inhibitors: Long-Term Functional and Cognitive Outcomes", JAGS, vol. 56, pp. 847-853, 2008.
Terry et al., "The Cholinergic Hypothesis of Age and Alzheimer's Disease-Related Cognitive Deficits: Recent Challenges and Their Implications for Novel Drug Development", JPET, vol. 306, pp. 821-827, 2003.
Guay, David, Trospium chloride; an update on a quaternary anticholinergic for treatment of urge urinary incontinence, Ther Clin Risk Manag., Jun. 2005; 1(2): 157-167, Minneapolis, MN, USA.
Langguth P, Kubis A, Krumbiegel G, et al. "Intestinal absorption of the quaternary trospium chloride: permeability-lowering factors and bioavailabilities for oral dosage forms". Eur J Pharm Biopharm. 1997;43:265-72, Elsevier Science.

* cited by examiner

FIXED DOSE COMBINATION OF CHOLINESTERASE INHIBITOR AND A QUATERNARY AMMONIUM ANTIMUSCARINIC AGENT TO TREAT NEURODEGENERATIVE COGNITIVE DISORDERS

FIELD OF THE INVENTION

The invention pertains to the field of cognitive treatments. More particularly, the invention pertains to improvements in cognitive function in patients treated with cholinesterase inhibitors in combination with quaternary ammonium anticholinergic muscarinic receptor antagonist.

BACKGROUND OF THE INVENTION

Neurodegenerative cognitive diseases impart costs on individuals and society in terms of loss of function, costs of care, and the personal loss of identity associated with pain and suffering. Such diseases or neurodegenerative cognitive disorders include, but are not limited to Alzheimer's Disease, Dementia with Lewy Body, Parkinson's Disease, and Progressive Supranuclear Palsy.

Cognitive neurodegeneration is a serious neurological condition that is very common in the elderly. By estimate, approximately one-third of people who live to be over 80 years of age will be diagnosed with some form of neurodegenerative cognitive disorder. Cognitive neurodegeneration can result from a variety of disease processes, such as, but not limited to:

Neurodegenerative Dementia:
  Alzheimer's Disease
  Pick's Disease
  Progressive Supranuclear Palsy
  Dementia with Lewy Bodies
  Parkinson's Disease
  Fronto-temporal Dementia
Vascular Diseases:
  Stroke
  Multi-infarct dementia
  Subarachnoid hemorrhage
  Head Trauma
Infections:
  Post-encephalitic dementia
  Syphilis
  Herpetic encephalitis
Congenital Abnormalities:
  Trisomy 21
Toxic Brain Injuries:
  Wernike Encephalopathy
  Krorsakoff psychosis
  Alcoholic amnesic syndrome
  Alcoholic dementia The primary result of this general condition is a universal decline in the intellectual function of the individual, usually resulting in significant impediments to normal daily functions. While there is currently no disease modifying treatment available for most forms of cognitive neurodegeneration, certain treatments are available to alleviate the symptoms and improve cognitive functioning to varying degrees, which can at least delay the need for institutionalizing these individuals.

It has been clinically determined that the decline of the neurotransmitter chemical acetylcholine in the brain is one of the primary mechanisms of declining mental function. Medications that can prevent or at least minimize the breakdown of acetylcholine in the brain provide significant improvement in the cognitive abilities of patients diagnosed with neurodegenerative cognitive disorders. These medications are commonly referred to as acetyl-cholinesterase inhibitors. However, as with any medication, there are side effects corresponding with administration of acetylcholinesterase inhibitors. For example, acetyl-cholinesterase inhibitors exacerbate urinary and fecal incontinence in patients administered these drugs. Other side effects include a reduced heart rate, sweating, vasodilation and increased bronchial secretions. Such side effects may be so uncomfortable for many elderly patients that the patient is unable to tolerate effective dosing of acetyl-cholinesterase inhibitors to successfully treat the neurodegenerative cognitive disorders.

Attempts to ameliorate these undesirable side effects in patients with cognitive neurodegeneration include the administration of, for example, antimuscarinic anti-cholinergic drugs (commonly called "anti-muscarinics"). These drugs block the peripheral stimulation of the acetylcholine receptors. Unfortunately, the use of these medications to treat the side effects of acetyl-cholinesterase inhibitors, previously mentioned, often contribute to cognitive neurodegeneration, which is what the acetyl-cholinesterase inhibitor is intended to treat in the first place. Thus, the benefits of using these drugs must be balanced with the risks of exacerbating the existing neurodegenerative cognitive disorder. As a result, many patients are either inadequately treated or go untreated.

Certain developmental disorders, particularly the Autism Spectrum Disorders, may share a neurodegenerative process, as suggested by the observed fact that normal development is often interfered with at some point after the first year of age. Increasing data suggests that neurodegenerative processes may reflect impaired clearance of endogenous molecules from the central nervous system. Suspected molecules include, but are not limited to, beta amyloid, alpha synuclein, tau, and numerous modifications of these molecules that occur through endogenous metabolic processes.

Despite the development of technologies for early detection of neurodegenerative processes, such as radio labeled antibodies against amyloid, the clinical role of such interventions has been limited by the fact that the justification for the cost of these diagnostic interventions is difficult in the absence of disease modifying therapies.

Over the years, researchers have studied the cognitive effects of anti-cholinergic drugs and have found that anti-cholinergic and anti-muscarinic drugs cause cognitive decline in the elderly and further cognitive decline in those already impaired. This effect is particularly true of drugs to treat urinary incontinence and overactive bladder. In fact, many practitioners refer to the dilemma regarding treatment of neurodegenerative cognitive disorders in combination with incontinence as choosing between "your brain versus your bladder". When prescribing medications, a practitioner has to work with their patients and their families and often decide whether to treat the incontinence caused by the medications being used to try to improve cognitive function, which would result in further detriment of cognitive function, or instead rely on alternative solutions to incontinence issues (including the often embarrassing use of adult diapers, or even institutionalization of the incontinent patient).

One severe type of cognitive impairment that often afflicts the elderly is referred to as acute delirium. The primary indicators are a pronounced change in mental status that rapidly fluctuates, the inability to maintain normal degrees of attention, disorganized thinking, and vacillating levels of consciousness. Acute delirium can often result from a severe medical illness, recent surgery, and use of several medications or interactions between various medications. The impact of acute delirium on patients is severe and often chronic, frequently leading to death.

While the neurological mechanism by which acute delirium occurs is not completely understood, like with other neurodegenerative cognitive disorders, the neurotransmitter acetylcholine is thought to play a significant role. In patients suffering from dementia, a decline in acetylcholine has been seen in post mortem studies. As with treatments for neurodegenerative cognitive disorders, the use of cholinesterase inhibiting medications has been determined to prevent, to varying degrees, the breakdown of acetylcholine in the brain. The undesirable side effects discussed above, however, outside the central nervous system (CNS), often result. In order to minimize these problems, the administration of drugs that block the peripheral system effects of cholinesterase inhibitors would be desirable. Unfortunately, in a manner similar to other neurodegenerative cognitive disorders, anti-cholinergics frequently contribute to the underlying problem by causing central nervous system toxicity.

SUMMARY OF THE INVENTION

A method of treating neurodegenerative cognitive disorders using cholinesterase inhibiting medications reduces or avoids the undesirable side effects discussed above. According to an embodiment, a method of the present invention includes a method for improving cognitive function in a human suffering from a neurodegenerative cognitive disorder. The method comprises administering to a patient a total daily dose of a cholinesterase inhibitor and a quaternary ammonium antimuscarinic compound, the total daily dose divided into one or more doses administered at least one hour before food intake. The quaternary ammonium antimuscarinic compound is administered in a first drug delivery element configured for rapid absorption into a body of the patient, and the cholinesterase inhibitor is administered in a second drug delivery element configured for a delayed absorption into the body of the patient.

In another embodiment, a method for improving cognitive function in a human suffering from a neurodegenerative cognitive disorder includes a first drug delivery element releasing a therapeutic amount of 2-8 mg of a quaternary ammonium antimuscarinic compound into a human body at a first initial time and at a first rate; and a second drug delivery element releasing a therapeutic amount of 3-48 mg of a cholinesterase inhibitor into the human body at a second initial time and at a second rate, wherein the first initial time is the same as the second initial time and the first rate is different than the second rate.

In another embodiment, a method for improving cognitive function in a human suffering from a neurodegenerative cognitive disorder comprises a first portion configured to release a therapeutic amount of 2-8 mg of a quaternary ammonium antimuscarinic compound into the human body. The first portion having a first dissolve rate, and a second portion configured to release a therapeutic amount of 3-48 mg of a cholinesterase inhibitor into a human body. The second portion having a second dissolve rate and the first dissolve rate is faster than the second dissolve rate.

DETAILED DESCRIPTION OF THE INVENTION

Figure 1:
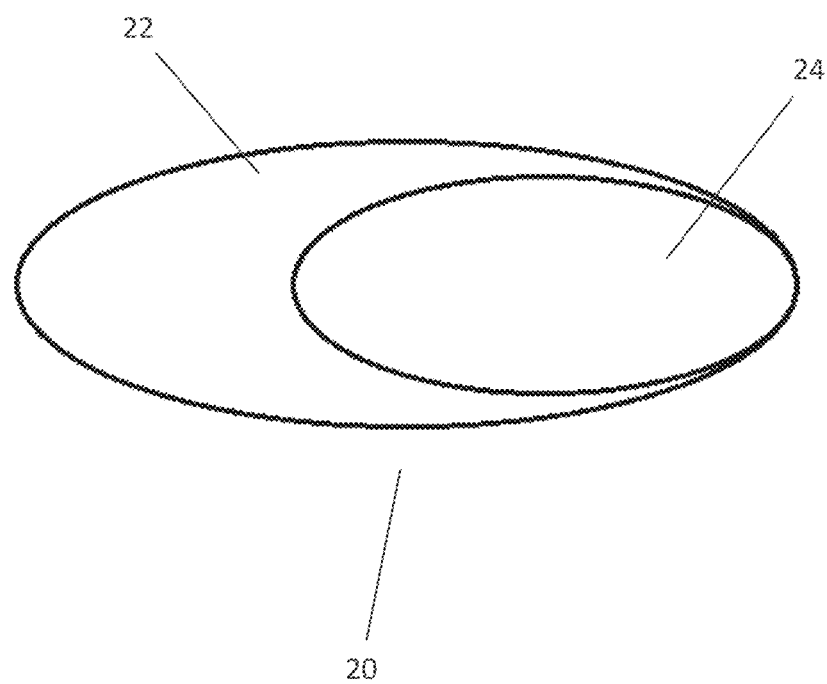
FIG. 1 shows an embodiment of a drug delivery element.

Patients suffering from various forms of neurodegenerative cognitive disorders, including acute delirium, can be treated with an effective amount of medication to reduce, minimize, or entirely alleviate these conditions without imposing upon the patients the undesired peripheral effects of urinary and/or fecal incontinence, nausea, bradycardia, bronchorrhea, and/or bronchospasm, which often coexist with these neurodegenerative cognitive disorders. The treatment can alter the disease progression of progressive dementias and other neurodegenerative cognitive disorders. The desired goal of treatment is to administer the most efficacious type and quantity of medication to treat the neurological condition without increasing the unwanted side effects of high doses of those medications. Appropriate treatment includes quaternary ammonium anti-cholinergic muscarinic receptor antagonists administered, at adequate levels, in combination with cholinesterase inhibitors, at doses that minimize the adverse effects inherent to unmitigated high doses of cholinesterase inhibitors that are used to treat neurodegenerative cognitive disorders. The treatment results in a modification of the disease, namely a slowing of the disease progression. In an embodiment, the quaternary ammonium anti-cholinergic muscarinic receptor antagonist administered to ameliorate the disease is glycopyrrolate and the acetyl-cholinesterase inhibitor administered to ameliorate the disease is rivastigmine. Rivastigmine blood serum concentrations between 0-25 ng/ml (nanograms per milliliter) are medically associated with improved symptom control in several neurodegenerative diseases. Generally, rivastigmine blood serum concentrations greater than 25 ng/ml are associated with the aforementioned adverse effects including urinary and/or fecal incontinence, nausea, bradycardia, bronchorrhea, bronchospasm, and orthostatic hypotension.

The quaternary ammonium anti-cholinergic muscarinic receptor antagonist prevents, or substantially ameliorates, the undesirable side effects of acetyl-cholinesterase inhibitors, which permits the administration of higher doses of acetyl-cholinesterase inhibitors than patients could otherwise tolerate. Quaternary ammonium anti-cholinergic muscarinic receptor antagonists can be administered to patients suffering from neurodegenerative cognitive disorders, in general, such as dementia, acute dementia and dementia with Lewy Bodies, because such compounds are excluded from the central nervous system. The patients can also be administered the cholinesterase inhibitor rivastigmine. Such treatment results in a marked improvement in cognitive function, in addition to an improvement in controlling the adverse effects of excessive acetylcholine including, but not limited to, urinary and/or fecal incontinence, nausea, bradycardia, bronchorrhea, and bronchospasm.

A benefit of using the anti-cholinergic muscarinic agents of the methods and compositions described herein is that the maximum dosing of the acetyl-cholinesterase inhibitor to effectively treat the neurodegenerative cognitive disorder afflicting the patient can be administered and maintained. Higher doses of acetyl-cholinesterase inhibitors may slow, or stop, the degenerative process through mechanisms that include improved clearance of toxic molecules. The use of the co-formulation of quaternary ammonium anti-cholinergic muscarinic receptor antagonist and cholinesterase inhibitors permits the administration of therapeutic dosages of cholinesterase inhibitors, thus maximizing the beneficial effect of the therapeutic drugs.

Suitable quaternary ammonium anti-cholinergic muscarinic receptor antagonists include the drugs trospium and glycopyrrolate, but not all antimuscarinic drugs are the same. One method of differentiating the various drugs in this category is by lipid solubility. It has been determined that quaternary ammonium compounds of the class of anti-cholinergic muscarinic agents having very low lipid solubility are desirable for use within the context of the methods and compounds described herein. As a result of their low lipophilicity (the ability of a compound to dissolve in a lipid medium), these molecules tend not to cross the blood/brain barrier as readily as those having higher lipid solubility. By not crossing the blood-brain barrier, these compounds do not interfere with the normal function of acetylcholine in the central nervous system, nor do they interfere with the beneficial effects of acetyl-cholinergic inhibitors for the treatment of neurodegenerative cognitive disorders. Further, these low lipid solubility quaternary ammonium anti-cholinergic muscarinic receptor antagonist drugs ameliorate the undesired peripheral effects from the use of acetyl-cholinesterase inhibitors, such as urinary and/or fecal incontinence, nausea, bradycardia, bronchorrhea, and bronchospasm.

The quaternary ammonium anti-cholinergic muscarinic agents for use in the methods described herein can include trospium and glycopyrrolate (non-quaternary anti-cholinergic agents include, but are not limited to, oxybutynin, tolterodine, darifenacin and solifenacin). Log P, a recognized parameter proportional to octanol/water partitioning coefficient, is a standard for measuring comparative solubility of a compound in a lipid compared to water. The comparative solubility of a drug molecule in water is the most important physical property that correlates with the capacity of the drug molecule to cross the blood/brain barrier and to interfere with the normal functioning of acetylcholine in the central nervous system. A low log P value represents low lipid solubility and low probability of crossing the blood/brain barrier. Both glycopyrrolate and trospium have a low log P based upon the nature of the chemical structure of glycopyrrolate and trospium. Comparatively, the standard anti-muscarinic drugs that are currently in use have a log P value as high as 6.076 (tolterodine). Trospium has a log P value of 0.78 and the calculated lipophilicity of glycopyrrolate is −75.75, thus making glycopyrrolate and trospium preferred compounds to achieve the therapeutic goals stated previously within the context of the embodiments described herein.

Glycopyrrolate (also known as glycopyrronium bromide) is a bromide salt with a quaternary ammonium counterion with the chemical name of 3-[cyclopentyl(hydroxy)phenylacetoxy]-1,1-dimethyl pyrrolidinium bromide, a molecular formula of $C_{19}H_{28}BrNO_3$ and a molecular weight of 398.34.

Trospium (also known as trospium chloride) is a quaternary ammonium salt with the chemical name of 3 (2 hydroxy-2,2 diphenylacetoxy)spiro[bicyclo[3.2.1]octane-8, 1' pyrrolidin]-1'-ium chloride. The molecular formula of trospium chloride is $C_{25}H_{30}ClNO_3$ and its molecular weight is 427.97. The chemical structure of trospium chloride is:

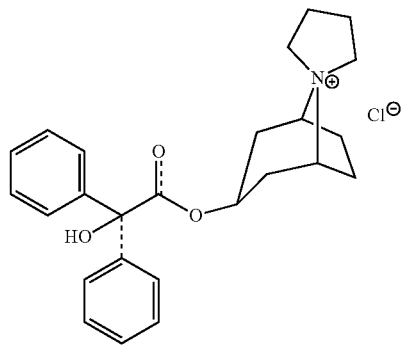

The quaternary ammonium anticholinergic muscarinic agents may be administered concurrently with any of the various acetyl-cholinesterase inhibitors used to treat neurodegenerative cognitive disorders. Such drugs include, but are not limited to:

donepezil
rivastigmine
galantamine
tacrine
physostigmine
pyridostigmine
neostigmine
ipidacrine
phenserine
icopezil
zanapezil
ambenonium
edrophonium
huperzine A
ladostigil In order to effectively treat patients suffering from neurodegenerative cognitive disorders that exhibit the unwanted adverse effects of excessive acetylcholine from a cholinesterase inhibitor including, but not limited to, urinary and/or fecal incontinence, nausea, bradycardia, bronchorrhea, bronchospasm, and orthostatic hypotension, quaternary ammonium anti-muscarinic agents can be combined with suitable acetyl-cholinesterase inhibitors. Both classes of drugs can be administered intravenously, intramuscularly ("parenterally"), or transdermally. Because patients with acute delirium are often confused and/or belligerent, these patients often refuse to take oral medications. In some cases, however, oral administration may be successfully achieved.

The quaternary ammonium antimuscarinic drugs (QAAM) provide benefits because of the drugs' ability to antagonize endogenous acetylcholine during periods of excessive acetylcholine production, or prolonged acetylcholine affect from physiologic and pharmacologic reasons. These compounds share the property that they do not appreciably penetrate the central nervous system (CNS), and glycopyrrolate bromide and trospium chloride have been particularly useful in treating patients in need of a peripheral anticholinergic effect on antimuscarinic receptors.

In patients with neurodegenerative cognitive disorders being treated with ACEI-QAAM, higher doses of all the acetylcholinesterase inhibitors are tolerated at least four times the usual monotherapy dose. For rivastigmine, the maximum monotherapy dose in the US is currently 12 mg/day orally or 9.5 mg/day transdermally (the FDA recently approved the use of 13.5 mg/day transdermally, but the maximum orally approved dose is still 12 mg/day). In some embodiments of the present invention, dosages up to 48 mg/day orally are used. In one embodiment, the daily dosage of the combination treatment is rivastigmine at 24-48 mg/day (or 17.9-39.9 mg transdermally) in combination with 1-2 mg of glycopyrrolate, orally, twice daily.

For patients exhibiting symptoms of dementia with Lewy bodies, a combination of rivastigmine and glycopyrrolate, for example, can be administered. In one embodiment, 12 mg to 48 mg/day of rivastigmine is administered orally, or 17.9 mg to 39.9 mg is administered transdermally. In another embodiment, 19 mg to 24 mg/day of rivastigmine is administered. In yet another embodiment, a minimum of 24 mg/day of rivastigmine is administered. In other embodiments, dosages of up to 48 mg/day orally of rivastigmine are used. In one embodiment, glycopyrrolate can be administered at the rate of 2 to 8 mg/day.

Generally, rivastigmine blood serum concentrations greater than 25 ng/ml are associated with the aforementioned adverse effects including urinary and/or fecal incontinence, nausea, bradycardia, bronchorrhea, bronchospasm, and orthostatic hypotension. Levels of this magnitude or greater may also be associated with more symptomatic improvement and disease modifying effects.

Administering quaternary ammonium antimuscarinic agents on an empty stomach can facilitate bioavailability. Comparatively, administering cholinesterase inhibitors, such as rivastigmine, with food can help delay the absorption of, and reduce the peak concentration of the cholinesterase inhibitors, which is associated with the previously mentioned adverse effects such as urinary and/or fecal incontinence, nausea, bradycardia, bronchorrhea, bronchospasm, and orthostatic hypotension. Accordingly, the coordinated absorption of quaternary ammonium antimuscarinic agents with cholinesterase inhibitors can help reduce or avoid the adverse effects of the cholinesterase inhibitors.

Taking the two drugs at separate time intervals related to food ingestion is inconvenient for patients suffering from neurodegenerative cognitive disorders. The separate administration of the quaternary ammonium antimuscarinic compound and the cholinesterase inhibitor to patient populations that present adherence difficulty, especially coordinated around food ingestion, can also be problematic. As previously discussed, patients with acute delirium are often confused and/or belligerent, such that these patients often refuse to take oral medications or forget. Simplifying oral dosing or the number of doses is beneficial in these instances. Coformulating glycopyrrolate and rivastigmine in a single dose yields greater ease of administration because separate administration of the two medications to patient populations that present adherence difficulty is minimized. The coformulation can be administered to the patient transdermally, in addition to orally or by other methods of administering. Transdermal administration, for example, can be easier with uncooperative or forgetful patients than oral administration.

In an embodiment, a method of improving cognitive function in a human suffering from a neurodegenerative cognitive disorder includes administering, orally, to a patient, a total daily dose of 3-48 mg of a cholinesterase inhibitor (rivastigmine), at a first initial time and at a first rate, and 2-8 mg of a quaternary ammonium antimuscarinic compound (glycopyrrolate) at a second initial time and at a second rate and the first initial time is different from the second initial time, and the first rate is different than the second rate. The total daily dose can be divided into individual doses administered at least one hour before food intake.

The total daily dose can be administered in one or more drug delivery elements that each release a therapeutic amount of 3-48 mg of a cholinesterase inhibitor, such as rivastigmine, into the human body and a therapeutic amount of 2-8 mg of a quaternary ammonium antimuscarinic compound, such as glycopyrrolate or 20-60 mg of trospium. Various forms of the drug delivery element can include a transdermal patch, a tablet, an injectable liquid, and a pill, tablet, or capsule. The drug delivery element can include these, as appropriate, or any other now-known or future-developed drug delivery structure.

According to methods of the invention, the cholinesterase inhibitor and the quaternary ammonium antimuscarinic compound can be administered in separate drug delivery elements, or as a single drug delivery element with multiple portions. If administered separately, according to some embodiments, the therapeutic amount of the quaternary ammonium anti-cholinergic muscarinic receptor antagonist can be administered to the patient orally, intravenously, or intramuscularly and the therapeutic amount of the acetylcholinesterase inhibitor can be administered to the patient either orally or transdermally. The cholinesterase inhibitor can be administered to the patient at least one hour before food intake.

FIG. 1 schematically illustrates a single drug delivery element 20 including a first portion 22 and a second portion 24 attached to or enclosed within the first portion 22. The first portion 22 can include quaternary ammonium antimuscarinic compound and the second portion 24 can include cholinesterase inhibitor. The first portion 22 can be rapidly dissolving, such as but not limited to a rapidly dissolving capsule (e.g., a gelatin capsule), and the second portion 24 can be an enclosed acid-resistant structure, such as but not limited to a capsule, configured for a delayed release. A hydroxypropylmethylcellulose (HPMC) capsule is an example of an enclosed acid-resistant structure. The delayed release of the second portion 24 can facilitate cholinesterase inhibitor acting on the small intestine.

In an embodiment, the drug delivery element 20 can be administered at least one hour before food intake. After administration, in some embodiments, the first portion 22 and the second portion 24 begin to dissolve concurrently. In these embodiments, though, the first portion 22 releases a therapeutic amount of 2-8 mg of a quaternary ammonium antimuscarinic compound into the human body according to a first dissolve rate, while the second portion 24 releases a therapeutic amount of 3-48 mg of a cholinesterase inhibitor into the human body according to a second dissolve rate. The first dissolve rate is faster than the second dissolve rate. The first portion 22 including a QAAM compound dissolves relatively quickly, while the second portion 24 including a cholinesterase component dissolves more slowly than the first portion 22. Thus, the slower dissolution of the second portion 24 enables the second portion 24 to be released after the patient has eaten, and the patient's body has absorbed, food.

In some embodiments, such as when the second portion 24 is enclosed within the first portion 22, the onset of dissolution of the second portion 24 is delayed from the onset of dissolution of the first embodiment 22. In this situation, the term "dissolve rate", as used herein, is an average dissolve rate calculated from the onset of dissolution of the first portion 22 or from the introduction of the drug delivery element 20 into the human body. In comparison, the term "instant dissolve rate" is intended to mean the dissolve rate at any given point in time. Similarly, the term "absorption rate" when applied to the QAAM compound and the cholinesterase inhibitor contained in the drug delivery element 20 is intended to mean an average rate of absorption calculated from the same point in time for both the QAAM compound and the cholinesterase inhibitor, such as the time the drug delivery element 20 is introduced into the human body or the time when the QAAM compound begins to be absorbed by the human body. The term "instant absorption rate" is intended to mean the absorption rate at any given point in time. Accordingly, whether the second portion 24 begins to dissolve later than the first portion 22 and then finishes dissolving later also, or whether the second portion 24 begins to dissolve at the same time as the first portion 22 but dissolves with a slower instant dissolve rate, such that it finishes dissolving later, the second portion 24 can be considered to have a slower dissolve rate than the first portion 22.

Patients treated with acetyl-cholinesterase inhibitors in combination with quaternary ammonium anti-cholinergic muscarinic agents (ACEI-QAAM) can be studied to collect data on the cognitive, affective, and functional improvement over time. Positive experimental data and results show delayed and reduced peak rivastigmine blood serum levels in patients using the method of the present invention, as reflected by the data displayed in FIG. 2A through FIG. 4.

Figure 2A:
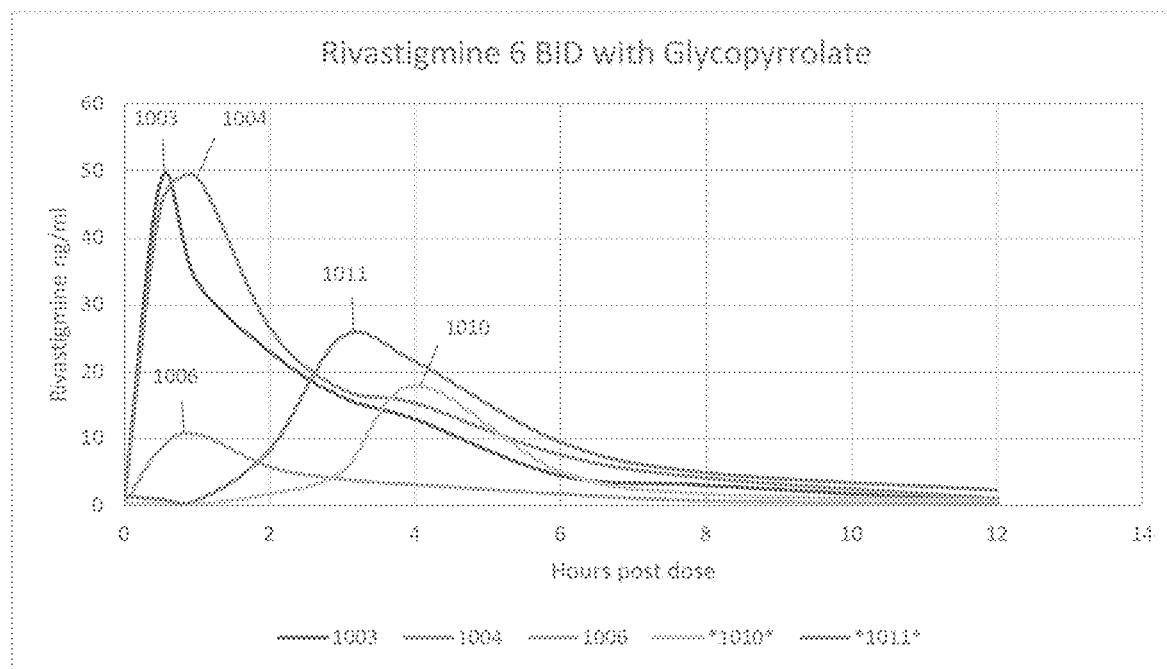
FIG. 2A shows a graph illustrating the results of a Phase 1 clinical trial of rivastigmine and glycopyrrolate administrations.

FIG. 2A compares rivastigmine blood serum concentration time profiles 12 hours post dose of five subjects: (a) two normal control subjects that were administered immediate release glycopyrrolate and increasing doses of rivastigmine simultaneously in a fasted state one hour prior to any food consumption; (b) two normal control subjects that were administered glycopyrrolate and rivastigmine separately with the glycopyrrolate administered while the subjects were in a fasting state, and with the rivastigmine administered to the subjects with food after one hour; and (c) a test subject that was administered the new co-formulated dosage of rivastigmine and glycopyrrolate one hour before consuming a meal.

In a Phase 1 trial, as shown in FIG. 2A, patient 1003 and patient 1004 were both normal control subjects that were administered immediate-release glycopyrrolate and increasing doses of rivastigmine, simultaneously, in a fasted state one hour prior to eating. Patient 1010 and Patient 1011 were administered the two medications separately with glycopyrrolate being administered in a fasting state and rivastigmine being administered with food approximately one hour later in order to ameliorate some of the side effects such as nausea. Patient 1006 was administered a lower dose of rivastigmine with glycopyrrolate simultaneously in a fasting state. The serum rivastigmine levels were obtained over the course of twelve hours post-administration. The results shown in FIG. 2A show that the high rivastigmine levels associated with adverse effects of the cholinesterase inhibitor, rivastigmine, were avoided with the giving the glycopyrrolate and rivastigmine doses separately in fasting and fed states respectively, 1 hour apart. and resulting coordinated absorption, of the quaternary ammonium anti-cholinergic muscarinic receptor antagonist, glycopyrrolate, as compared to the coadministration, in patients 1003, and 1004, of glycopyrrolate and rivastigmine in a fasted state. Comparatively, the separate administration of glycopyrrolate, while the patients 1010 and 1011 were in a fasted state, and rivastigmine, and while the patients were fed, was attenuated, showing the delayed peak serum concentration associated with lower peak rivastigmine levels and reduced adverse effects, particularly nausea. It was proposed that with the coformulation, patients can take one dose of the medication in a single drug delivery element and eliminate the separate administration of two medications to patient populations that present adherence difficulty. The coformulation allows this singular does and still approximates the rivastigmine blood serum concentrations seen with separate administration of the components in fed and fasting states. Time profile of patient 1006, 10 ng/ml, obtained with the co-formulated drug delivery element taken in a fasting state, displays absorption kinetics similar to that of the separately administered components.

Figure 2B:
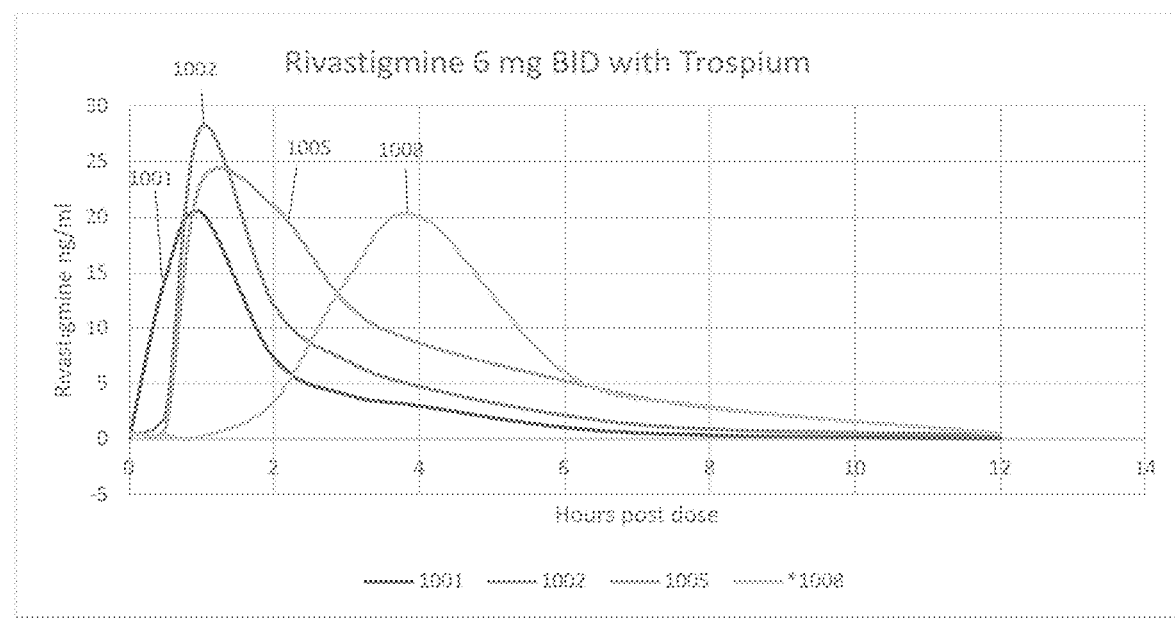
FIG. 2B shows a graph illustrating the results of a Phase 1 trial with rivastigmine and trospium administrations.

FIG. 2B compares the rivastigmine blood serum concentration time profiles, in normal control subjects, obtained with: (a) concurrent administration of 6 mg rivastigmine and 20 mg trospium, a different quaternary ammonium antimuscarinic agent from glycopyrrolate in a fasting state; (b) separated administration of 6 mg rivastigmine and 20 mg trospium in a fasting state, and 6 mg of rivastigmine in a fed state one hour later; and (c) the novel co-formulated drug dosage administration simultaneously, in an embodiment of the present invention, taken (BID) twice per day. Patients 1001, 1002, and 1005 were administered trospium and rivastigmine simultaneously in a fasting state. Subject 1008 was administered trospium and rivastigmine in fasting and fed states, respectively. The rivastigmine blood serum concentrations illustrated in FIG. 2B show attenuated peak rivastigmine levels achieved by taking the medication with food, similar to that seen with glycopyrrolate and rivastigmine administered separately.

Figure 3:
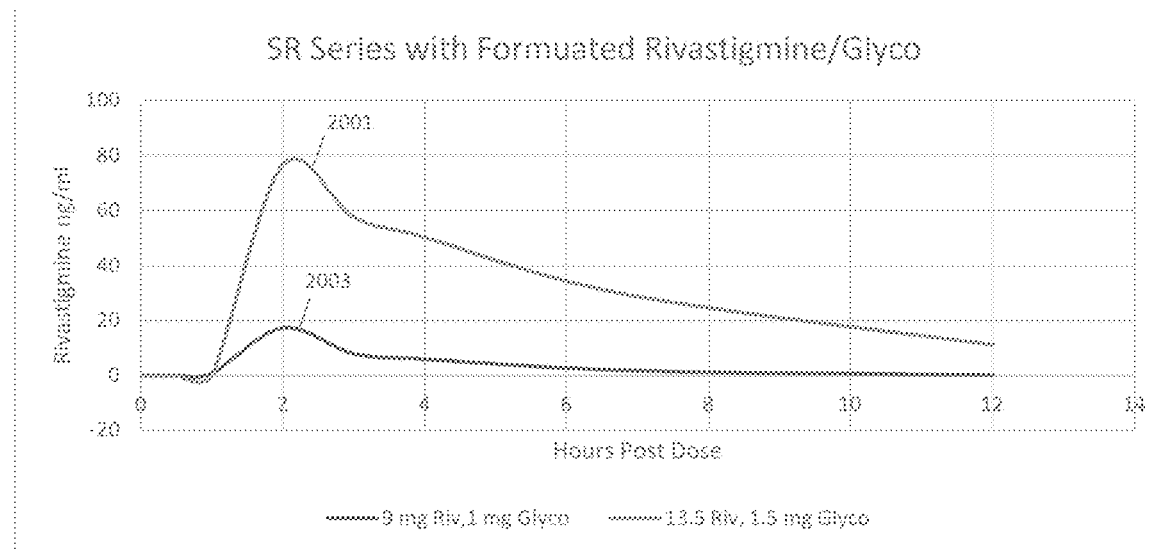
FIG. 3 shows a graph depicting a rivastigmine blood serum concentration time profile of a patient after ingesting the co-formulation of rivastigmine/glycopyrrolate taken one hour before eating food.

FIG. 3 displays the effects of the co-formulation of a rivastigmine/glycopyrrolate administration in a single control subject. This co-formulation was administered in the morning one hour before food was consumed on separate days in two different doses. In an embodiment, the drug delivery system is a co-formulated capsule having 0.5 mg glycopyrrolate and 4.5 mg rivastigmine. With this specific embodiment, doses can be multiples of 0.5 mg glycopyrrolate and 4.5 mg rivastigmine and can be administered two, three, or four times per day depending upon the disease state. In other embodiments, the ratio of the quaternary ammonium antimuscarinic/cholinesterase inhibitor compound my vary in order to achieve a dosing regimen optimized to the patient and the disease being treated.

FIG. 3 compared with FIGS. 2A and 2B demonstrates that the serum concentration-time profile of rivastigmine achieved with the single dosing of the compounded drug delivery system is similar to that achieved by separate administration of the components in fasting and fed states. Dosing with the co-formulated drug delivery system was not associated with the nausea associated with the simultaneous administration of both components in a fasting state.

Figure 4:
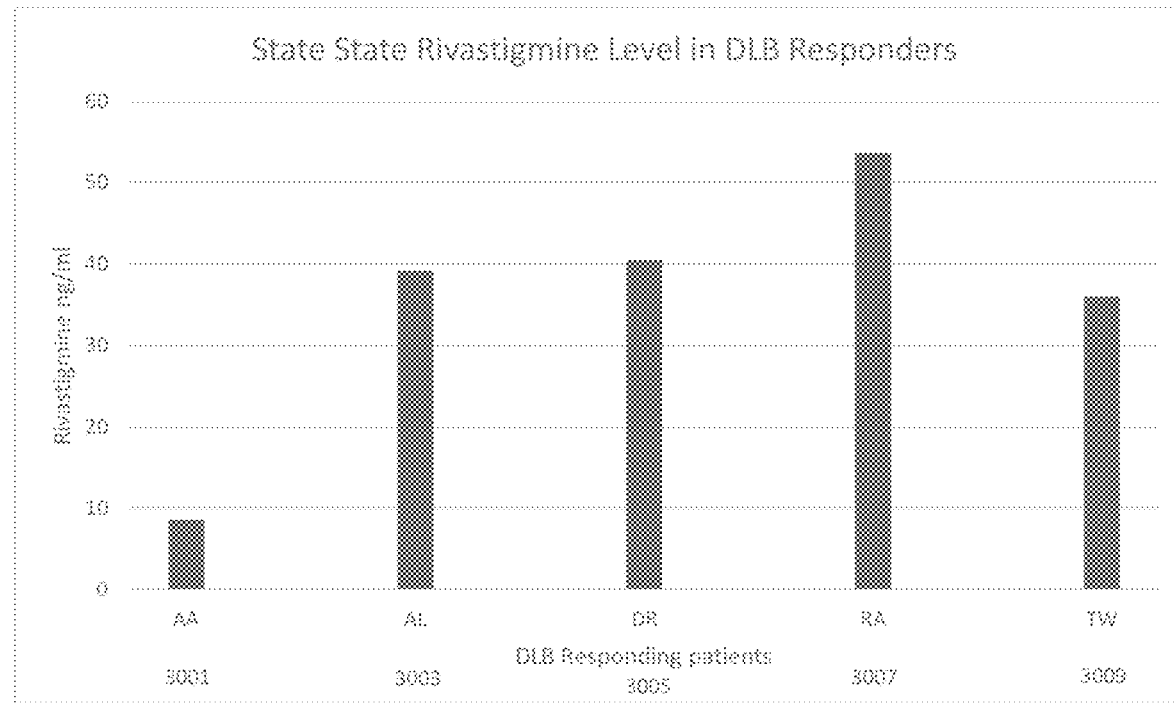
FIG. 4 shows a bar graph displaying a rivastigmine steady state blood serum concentration level of patients afflicted with Dementia with Lewy bodies, wherein the patients have shown disease-modifying effects.

FIG. 4 exhibits the steady state blood serum rivastigmine levels in patients 3001, 3003, 3005, 3007, 3009 that have dementia with Lewy bodies and had demonstrated a reduction in the rate of cognitive decline over years with combined rivastigmine and glycopyrrolate administered separately. These subjects did not display adverse effects despite high doses of rivastigmine—36-42 mg/day orally, and 39.9 mg/day transdermally. Patient 3009 was administered two co-formulated capsules of 0.5 mg glycopyrrolate and 4.5 mg glycopyrrolate four times per day, one hour before eating, for a daily dose of rivastigmine of 36 mg. Based upon the concentration-time curves, it can be derived that the co-formulation can maintain a similar concentration of rivastigmine throughout the dosing interval.

The constellation of symptoms in dementia with Lewy Bodies includes vivid hallucinations, falling, precipitous drops in blood pressure with standing (orthostatic hypotension). Rapid fluctuations in consciousness and orientation occur and there is a commonly a sleep disturbance (Rapid Eye Movement Sleep Behavioral Disturbance). The patients are often intolerant of drugs commonly used for psychosis (Neuroleptic Sensitivity Syndrome). The patients have variable moods with a predisposition to depression and varying degrees of symptoms similar to Parkinson's disease. The co-formulation, in a single drug delivery element, can be more conveniently administered to patients that have dementia with Lewy bodies, and can be better tolerated by these patients as well.

Dementia with Lewy Bodies is a progressive dementing disease with some features of Parkinson's disease. Dementia with Lewy Bodies progresses faster than Alzheimer's Disease and provides an opportunity to observe a change in the deterioration of neurodegenerative cognitive ability over time (Olichney J M et al. "Cognitive Decline is Faster in Lewy Body Variant than in Alzheimer's Disease". Neurology 1998; 51 (2)351, herein incorporated by reference). Cholinesterase inhibition, particularly with rivastigmine, is the most efficacious treatment for Dementia with Lewy Bodies.

Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. A drug delivery element comprising:
   a first portion configured to release a therapeutic amount of 2-8 mg of a quaternary ammonium antimuscarinic compound into the human body, the first portion having a first dissolve rate; and
   a second portion configured to release a therapeutic amount of 3-48 mg of a cholinesterase inhibitor into a human body, the second portion having a second dissolve rate,
   wherein the first dissolve rate is faster than the second dissolve rate.

2. The drug delivery element of claim 1, wherein the cholinesterase inhibitor includes rivastigmine, and the quaternary ammonium antimuscarinic compound includes glycopyrrolate or trospium.

3. The drug delivery element of claim 1, wherein the first portion is
   configured for rapid dissolution, and the second portion is enclosed, acid resistant, and
   configured for delayed release in a small intestine of the human body.

4. The drug delivery element of claim 1, wherein the first portion includes a gelatin capsule and the second portion includes a hydroxypropylmethylcellulose capsule.

5. The drug delivery element of claim 1, wherein the first portion is a first capsule and the second portion is a second capsule contained within the first capsule.

* * * * *